US005714344A

United States Patent [19]
Ollert et al.

[11] Patent Number: 5,714,344
[45] Date of Patent: Feb. 3, 1998

[54] PROTEASE-DERIVATIZED CVF

[75] Inventors: Markus W. Ollert; Patrick Ziegelmüller; Thomas Grunwald; Reinhard Bredehorst; Carl-Wilhelm Vogel, all of Hamburg, Germany

[73] Assignee: Georgetown University, Washington, D.C.; a part interest

[21] Appl. No.: 118,674

[22] Filed: Sep. 10, 1993

Related U.S. Application Data

[63] Continuation-in-part of Ser. No. 43,747, Apr. 7, 1993, abandoned.
[51] Int. Cl.$^6$ .............................. C12P 21/06; C12N 9/50; C07K 14/46
[52] U.S. Cl. .................... 435/68.1; 435/212; 530/350
[58] Field of Search .................... 435/68.1, 212; 530/350

[56] References Cited

U.S. PATENT DOCUMENTS

| | | | |
|---|---|---|---|
| 4,289,690 | 9/1981 | Pestka et al. | 530/351 |
| 4,727,028 | 2/1988 | Santerre et al. | 435/240.2 |

OTHER PUBLICATIONS

Hadding, U. et al. (1978) "Influence of elastase-like protease on guinea pig C3, factor B of the properdin system and the tumor cell line EL4" Neutal Proteases Hum. Polymorphonucl. Leukocytes, (Proc. Int. Symp. of 1977), pp. 287–291, abstract only.

E. Teicher et al, *Immunochemistry*, (1973), 10, pp. 265–271, "The Role of Specific Amino Acid Residues in the Antigenic Reactivity of the Loop Peptide of Lysozyme".

R. Arnon et al, *Proc. Nat. Acad. Sci. USA*, (1971), 68, pp. 1450–1455, "Antibodies Reactive with Native Lysozyme Elicited by a Completely Synthetic Antigen".

D. C. Fritzinger et al, *Proc. Nat. Acad. Sci. USA*, (1994), 91, pp. 12775–12779, "Molecular Cloning and Derived Primary Structure of Cobra Venom Factor".

C-W. Vogel et al, *Journal of Immunological Methods*, (1984), 73, pp. 203–220, "Cobra Venom Factor: Improved Method for Purification and Biochemical Characterization".

D. C. Fritzinger et al, "Complete Structure of Cobra Complement Component C3 mRNA", Abstract, 15th International Congress of Biochemistry, Jerusalem, Israel, Aug. 4–8, 1991.

Poster Material (9 sheets) Presented at Cambridge, England, Sep. 1991 and at Anaheim, California, on Tuesday Apr. 7, 1992. See Fritzinger et al, *Complement and Inflation*, (1991), 8, p. 152 and Fritzinger et al, *FASEB Journal*, (1992), 4, p. A1903.

D. Gowda et al, *Molecular Immunology*, (1992), 29, pp. 335–342, "Structure of the Major Oligosaccharide of Cobra Venom Factor".

C.W. Vogel et al, *Developmental and Comparative Immunology*, (1985), 9, pp. 311–325, "The Cobra Complement System: I. The Alternative Pathway of Activation".

E. Petrella et al, *Journal of Immunological Methods*, (1987), 104, pp. 159–172, "Antibody Conjugates with Cobra Venom Factor. Synthesis and Biochemical Characterization".

C-W. Vogel et al, *Journal of Immunology*, (1984), 133, pp. 3235–3241, "Cobra Venom Factor: Structural Homology with the Third Component of Human Complement".

A. Grier et al, *The Journal of Immunology*, (1987), 139, pp. 1245–1252, "Cobra Venom Factor and Human C3 Share Carbohydrate Antigenic Determinants".

S. Kunkel et al, Reprinted from *Immunology III*, (1985), pp. 106–116, "Chapter 6—The Complement System".

M. O'Keefe et al, *The Journal of Biological Chemistry*, (1988), 263, pp. 12690–12697, "A Novel Cleavage Product of Human Complement Component C3 with Structural and Functional Properties of Cobra Venom Factor".

C.W. Vogel et al, *Proc. Natl. Acad. Sci*, (1981), 78, pp. 7707–7711, "Induction of Immune Cytolysis: Tumor–Cell Killing by Complement is Initiated by Covalent Complex of Monoclonal Antibody and Stable C3/C5 Convertase".

C.W. Vogel et al, *Haematology and Blood Transfusion*, (1985), 29, pp. 514–517, "In Vivo Studies with Covalent Conjugates of Cobra Venom Factor and Monoclonal Antibodies to Human Tumors".

C.W. Vogel, *Immunology and Allergy Clinics of North America*, (1991), 11, pp. 277–299, "Complement, A Biologic Effector Mechanism for Tumor Cell Killing".

H. Juhl et al, *Molecular Immunology*, (1990), 27, pp. 957–964, "Complement Killing of Human Neuroblastoma Cells: A Cytotoxic Monoclonal Antibody and Its F(ab)'$_2$–Cobra Venom Factor Conjugate are Equally Cytotoxic".

C.W. Vogel, *Handbook of Natural Toxins* (A. T. Tu, editor), (1991), 5–*Reptile Venoms and Toxins*, pp. 147–188, "Cobra Venom Factor: The Complement–Activating Protein of Cobra Venom".

D. Fritzinger et al, presented at 6th Pan–American Biochemistry Congress, Sao Paulo, Brazil, (1990), "Molecular Cloning of Cobra Venom Factor and Cobra Complement Component C3: Structural Homology with Human C3".

R. Mierendorf et al, *Methods in Enzymology*, (1987), 152, pp. 458–469, "Gene Isolation by Screening λgt11 Libraries with Antibodies".

D. Weir et al (editors), *Handbook of Experimental Immunology in Four Volumes—vol. 1: Immunochemistry*, (1986) pp. 39.34–39.49.

C. Beukelman et al, *Journal of Immunological Methods*, (1987), 97, pp. 119–122, "A One–Step Isolation Procedure of Phospholipase A$_2$–Free Cobra Venom Factor by Fast Protein Liquid Chromatography".

(List continued on next page.)

*Primary Examiner*—Robert A. Wax
*Assistant Examiner*—Kawai Lau
*Attorney, Agent, or Firm*—Oblon, Spivak, McClelland, Maier & Neustadt, P.C.

[57] ABSTRACT

A novel functionally active derivative of cobra venom factor is described in which the β-chain has been cleaved by treatment with a protease. Gel electrophoretic analyses of the purified derivative revealed the absence of an intact β-chain and a decrease of the molecular weight.

31 Claims, 10 Drawing Sheets

OTHER PUBLICATIONS

E. Petrella et al, *Complement and Inflammation*, (1989), 6, pp. 386–387, "Purification of Cobra C3: Initial Characterization and Comparison to Cobra Venom Factor".

B. Alberts et al, *Molecular Biology of The Cell* (2nd edition), (1989), pp. 265–266, Garland Publishing.

P. Sakiyalak et al, *Mol. Immunol.*, (1993), 30, p. 49, "Synergistic Effect of Antibody (Ab) and Complement (C) Depletion on Cardiac Xenograft (Xg) Survival in Nonhuman Primates".

D. Fritzinger et al, *Complement and Inflammation*, (1991), 8, p. 152, (Abstract No. 76), "Sequence Analysis of Cobra Venom Factor mRNA Reveals the Existence of Two Different mRNA Species".

D. Fritzinger et al, *Complement and Inflammation*, (1991), 8, p. 152, (Abstract No. 77), "Complete Structure of Cobra Complement Component C3 mRNA".

D. Fritzinger et al, *The FASEB Journal*, (1992), p. A1453, (Abstract No. 2993), "Complete Sequence of Two Different Cobra Venom Factor cDNAs".

D. Fritzinger et al, *The FASEB Journal*, (1990), 4, p. A1903), "Molecular Cloning of Cobra Venom Factor and Cobra C3: Structural Homology with Human C3".

D. Fritzinger et al, *J. Immunol.*, (1992), 149, pp. 3554–3562, (Abstract No. 93056528), "Primary Structure of Cobra Complement Component C3".

Federation Proceedings, vol. 36, No. 3, 1977, p. 1245, entry No. 5169, Brian J. Johnson, et al., "Studies on the Purification and Fragmentation of Cobra Venom Factor".

Journal of Immunological Methods, vol. 30, 1979, pp. 105–117, M.B. Pepys, et al., "An Improved Method for the Isolation from Naja Naja Venom of Cobra Factor (CoF) Free of Phospholipase A".

Molecular Immunology, vol. 18, 1981, pp. 125–133, Gosta Eggertsen, et al., "Molecular Characterization of the Complement Activating Protein in the Venom of the Indian Cobra (Naja N. Siamensis)".

Proceedings of the National Academy of Sciences USA, vol. 78, No. 12, Dec. 1981, pp. 7707–7711, Carl–Wilhelm Vogel, et al., "Induction of Immune Cytolysis: Tumor–Cell Killing by Complement is Initiated by Covalent Complex of Monoclonal Antibody and Stable C3/C5 Convertase".

Molecular Immunology, vol. 27, No. 10, pp. 957–964, 1990, Hartmut Juhl, et al., "Complement Killing of Human Neuroblastoma Cells: A Cytotoxic Monoclonal Antibody and Its F(ab)'2–Cobra Venom Factor Conjugate are Equally Cytotoxic".

Kirschfink, M. et al. (May 1988) "Binding and activation of C4 and C3 on the red cell surface by non–complement enzymes" Molec. Immunol. 25(5):505–512.

Von Zabern, I. et al. (1982) "Chain structure of cobra venom factor from *Naja naja* and *Naja haje* venom" *Scan. J. Immunol.* 15(4):357–362.

```
                                                             → β-Kette
CVF 1  1218  Q N F Y G E T Y G Q T Q A T V M A F Q A L A E Y↓E I Q M P T H K D L N L D I T I  1257
CVF1   1258  E L P D R E V P I R Y R I N Y E N A L L A R T V E T K L N Q D I T V T A S G D G  1297
                                             ①→          *CHO
CVF 1  1298  K A T M T I L T F Y N A Q L Q E K A N V C N K P H L N V S V E N I H L N A M G A  1337
                             ②→
CVF 1  1338  K G A L M L K I C T R Y L G E V D S T M T I I D I S M L T G F L P D A E D L T R  1377
                                                                            ←②
CVF 1  1378  L S K G V D R Y I S R Y E V D N N M A Q K V A V I I Y L N K V S H S E D E C L H  1417
                                                           ←①
CVF 1  1418  F K I L K H F E V G F I Q P G S V K V Y S Y Y N L D E K C T K F Y H P D K C T C  1457
                       ③→   ←③  ⊙       ④→                                      ⑤→
CVF 1  1458  L L N K I C I G N V C R C A G E T C S S L N H Q E R I D V P L Q I E K A C E T N  1497
CVF 1  1498  V D Y V Y K T K L L R I E E Q D C N D I Y V M D V L E V I K Q G T D K N R R A K  1537
                              ←④
CVF 1  1538  T H Q Y I S Q R K C Q E A L N L K V N D D Y L I W G S R S D L L P T K D K I S Y  1577
                                      ⑥→             ←⑥
CVF 1  1578  I I T K N T W I E R W P H E D E C Q E E E F Q K L C D D F A Q F S Y T L T E F G  1617
            ←⑤
CVF 1  1618  C P T                                                                            1620
```

FIG. 10

PROTEASE-DERIVATIZED CVF

This application is a Continuation-In-Part of U.S. patent application Ser. No. 08/043,747 filed Apr. 7, 1993, now abandoned which is incorporated herein by reference.

BACKGROUND OF THE INVENTION

1. Field of the Invention

The present invention relates to functionally active derivatives of cobra venom factor (CVF) generated by treatment with a protease, a method for producing such derivatives of CVF, and antibody conjugates of such CVF derivatives.

2. Discussion of the Background

When CVF is added to human or other mammalian serum, it activates complement and leads to complement consumption. In serum, CVF binds to factor B of the alternative pathway (Müller-Eberhard et al., Arch. Pathol., 82:205-217 (1966); Müller-Eberhard and Fjelstrom, J. Immunol., 107:1666-1672 (1971); Götze and Müller-Eberhard, J. Exp. Med., 134:90s-108s (1971); Goodkofsky and Lepow, J. Immunol., 107:1200-1204 (1971); Brade et al., J. Immunol., 109:1174-1181 (1972); Alper et al., J. Exp. Med., 137:424-437 (1973); Lynen et al., Hoppe-Seyler's Z. Physiol. Chem., 354:37-47 (1973)). When factor B is in complex with CVF, factor B is cleaved by factor D into Ba, the activation peptide that is released, and Bb that remains bound to CVF (Müller-Eberhard and Götze, J. Exp. Med., 135:1003-1008 (1972); Hunsicker et al., J. Immunol., 110:128-137 (1973); Lesavre et al., J. Immunol., 123:529-534 (1979)). The bimolecular complex, CVF,Bb, is a C3 convertase which cleaves C3 (Müller-Eberhard and Fjelstrom, J. Immunol., 107:1666-1672 (1971); Vogt et al., Hoppe-Seyler's Z. Physiol. Chem., 355:171-183 (1974); Vogel and Müller-Eberhard, J. Biol. Chem., 257:8292-8299 (1982)). In addition to its binding site for factor B, CVF has a binding site for C5 (Von Zabern et al., Immunology, 157:499-514 (1980). C5, when bound to CVF, becomes susceptible to cleavage by the CVF,Bb enzyme. Accordingly, the CVF,Bb enzyme has not only C3-cleaving activity but also C5-cleaving activity and is referred to as C3/C5 convertase (DiScipio et al., J. Biol. Chem., 258:10629-10636 (1983); Petrella et al., J. Immunol. Methods, 104:159-172 (1987)).

The formation and function of the CVF-dependent C3/C5 convertase are analogous to the formation and function of the mammalian C3b-dependent C3/C5 convertase that is formed during activation of the alternative pathway (Götze and Müller-Eberhard, J. Exp. Med., 134:90s-108s (1971); Lachmann and Nicol, Lancet, 1:465-467 (1973); Vogt et al., Immunochemistry, 14:201-205 (1977); Lachmann, Behring Inst. Mitt., 63:25-37 (1979); Smith et al., J. Exp. Med., 159:324-329 (1984)). Both enzymes, however, exhibit important functional differences. The C3b,Bb enzyme is subject to rapid and efficient regulation by factors H and I, while the CVF,Bb enzyme and CVF are completely resistant to the regulatory actions of factors H and I (Lachmann and Halbwachs, Clin. Exp. Immunol., 21:109-114 (1975); Alper and Balavitch, Science, 191:1275-1276 (1976); Nagaki et la., Int. Archs. Allergy Appl. Immunol., 57:221-223 (1978)). Furthermore, the C3b, Bb enzyme is very short-lived with a half-life of the decay-dissociation of 1.5 minutes at 37° C. (Medicus et al., J. Exp. Med., 144:1076-1093 (1976); Pangburn and Müller-Eberhard, Biochem. J., 235:723-730 (1986)), whereas the CVF,Bb enzyme is rather stable with a half-life of 7 hours (Vogel and Müller-Eberhard, J. Biol. Chem., 257:8292-8299 (1982)).

Depletion of complement activity is a consequence of the addition of CVF to serum. When CVF is added to serum, the CVF,Bb enzyme forms utilizing the alternative pathway components, factor B and factor D. The physico-chemical stability of the CVF,Bb enzyme and its absolute resistance to the regulatory proteins, factor H and factor I, lead to continuous cleavage of C3 and C5. The generated C5b consumes the terminal complement components in plasma by formation of the macromolecular membrane attack complex (MAC). The MAC that forms in plasma is bound by the regulatory plasma protein vitronectin and is then referred to as the SC5b-9 complex (Podack and Tschopp, Mol. Immunol., 21:589-603 (1984)). Furthermore, any CVF freed from the CVF,Bb enzyme by spontaneous decay-dissociation can be reused to form a new CVF,Bb enzyme as long as factor B is still present. The final result of complement activation by CVF, therefore, is the depletion of the serum complement activity by consumption of C3, C5, C6, C7, C8, C9, and factor B (Maillard and Zarco, Ann. Inst. Pasteur., 114:756-774 (1968); Birdsey et al., Immunology, 21:299-310 (1971); Bauman, J. Immunol., 120:1763-1764 (1978)). In vivo, complement depletion is rather rapid, reaching maximal depletion within hours (Maillard and Zarco, Ann. Inst. Pasteur., 114:756-774 (1968)). The complement activity will remain low for one to several days, dependent on the amount of CVF injected. However, resynthesis of consumed complement components occurs, and normal complement activity is restored within 5-10 days (Vogel and Müller-Eberhard, J. Immunol. Methods, 73:203-220 (1984)). Several examples of studies in which the role of complement was investigated by depleting complement with CVF are listed in Table 1, shown below.

Table 1

| Complement Depletion Studies with CVF. | |
|---|---|
| Subject Studied | Reference |
| Uptake of mycobacteria by monocytes | Swartz et al., Infect. Immun., 56:2223-2227 (1988) |
| Renal xenograft rejection | Kemp et al., Transplant Proc., 6:4471-4474 (1987) |
| Feline leukemia | Kraut et al., Am. J. Vet. Res., 7:1063-1066 (1987) |
| Cardiac xenograft survival | Adachi et al., Transplant Proc., 19:1145-1148 (1987) |
| Antitumor mechanism of monoclonal antibody | Welt et al., Clin. Immunol. Immunopathol. 45:215-229 (1987) |
| Pulmonary vascular permeability | Johnson et al., J. Appl. Physiol., 6:2202-2209 (1986) |
| Glomerular injury and proteinuria | Rehan et al., Am. J. Pathol. 111:57-66 (1986) |
| Fowlpox virus infection | Ohta et al., J. Virol., 2:670-673 (1986) |
| Endotoxin-induced lung injury | Flick et al., Am. Rev. Respir. Dis. 135:62-67 (1986) |
| Immunologically mediated otitis media | Ryan et al., Clin. Immunol. Immunopathol., 40:410-421 (1986) |
| Antigen-induced arthritis | Lens et al., Clin. Exp. |

Table 1-continued

Complement Depletion Studies with CVF.

| Subject Studied | Reference |
|---|---|
| | Immunol., 3:520–528 (1984) |
| Humoral resistance to syphilis | Azadegan et al., Infect. Immun., 3:740–742 (1984) |
| Acute inflammation induced by Escherichia coli | Kopaniak and Movat, Am. J. Pathol., 110:13–29 (1983) |
| Cutaneous late-phase reactions | Lemanske et al., J. Immunol., 130:1881–1884 (1983) |
| Bleomycin-induced pulmonary fibrosis | Phan and Thrall, Am. J. Pathol., 107:25–28 (1982) |
| Delayed hypersensitivity reactions | Jungi and Pepys, Immunology, 42:271–279 (1981) |
| Vitamin $D_2$-induced arteriosclerosis | Pang and Minta, Artery, 2:109–122 (1980) |
| Macrophage activation by Corynebacterium | Ghaffar, J. Reticuloendothel. Soc., 27:327–335 (1980) |
| Allergic encephalomyelitis | Morariu and Dalmasso, Ann. Neurol., 5:427–430 (1978) |
| Effect of complement depletion on IgG and IgM response | Martinelli et al., J. Immunol., 121:2043–2047 (1978) |
| Myocardial necrosis after coronary artery occlusion | Maroko et al., J. Clin. Invest., 3:661–670 (1978) |
| Resistance to ticks | Wikel and Allen, Immunology, 34:257–263 (1978) |
| Lung clearance of bacteria | Gross et al., J. Clin. Invest., 62:373–378 (1978) |
| Immune complex disease in the lung | Roska et al., Clin. Immunol. Immunopathol., 8:213–224 (1977) |
| Migration of T and B lymphocytes into lymph | Spry et al., Immunology, 32:947–954 (1977) |
| Leukocyte circadian variation | Hoopes and McCall, Experientia, 2:224–226 (1977) |
| Initial gingivitis | Kahnberg et al., J. Periodont. Res., 5:269–278 (1976) |

The property of the CVF,Bb enzyme to exhaustively activate complement has also been exploited for the selective killing of tumor cells by coupling of CVF to monoclonal antibodies with specificity for surface antigens of tumor cells. Antibody conjugates with CVF will target CVF to the cell surface, at which the CVF,Bb enzyme forms from complement factors B and D of the host complement system. The antibody-bound and, therefore, cell surface-bound CVF, Bb enzyme will continuously activate C3 and C5 and elicit complement-dependent target cell killing. Antibody conjugates with CVF have been shown to kill human melanoma cells (Vogel and Müller-Eberhard, Proc. Natl. Acad. Sci. U.S.A., 78:7707–7711 (1981); Vogel et al., Modern Trends in Human Leukemia VI, Neth et al. eds, Springer Verlag, Berlin, pp. 514–517 (1985)), human lymphocytes and leukemia cells (Müller et al., Br. J. Cancer, 54:537 (1986); M üller and Müller-Ruchholtz, Immunology, 173:195–196 (1986); Müller and Müller-Ruchholtz, Leukemia Res., 11:461–468 (1987)), and human neuroblastoma cells (Juhl et al., Proc. Am. Assoc. Cancer Res., 30:392 (1989); Juhl et al., Mol. Immuno., 27:957–964 (1990)).

CVF from the Asian cobra (Naja naja) is a three-chain glycoprotein. The $M_r$ of CVF is 136,000 as determined by equilibrium sedimentation (Vogel and Müller-Eberhard, Immunol. Methods, 73:203–220 (1984)). Sodium dodecyl sulfate-polyacrylamide gel electrophoresis (SDS-PAGE) yields a $M_r$ of 149,000 as the sum of the α-chain ($M_r$ 68,500), β-chain ($M_r$ 48,500), and γ-chain ($M_r$ 32,000). Dependent on the gel electrophoretic system employed, several authors have demonstrated size heterogeneity of the γ-chain in their CVF preparations (Pepys et al., J. Immunol. Methods, 30:105–177 (1979); Eggertsen et al., Mol. Immunol., 18:125–133 (1981); Von Zabern et al., Scand. J. Immuno., 15:357–362 (1982); Vogel and Müller-Eberhard, J. Immunol. Methods, 73:203–220 (1984)). The molecular basis for this size heterogeneity is not fully understood. Most likely it is due to differential processing at the COOH-terminus of the γ-chain, since Eggertsen et al. Mol. Immunol., 18:125–133 (1981)) found a consistent $NH_2$-terminal amino acid sequence of the γ-chain. Table 2 shows the amino acid compositions of CVF and its three isolated chains (Vogel and Müller-Eberhard, J. Immunol. Methods, 73:203–220 (1984)).

TABLE 2

Amino Acid Composition of CVF and its Three Chains.

| Amino acid | From complete analysis[a] | From gel analysis[b] | Sum of α + β + γ chains[b] | α-Chain[b] | β-Chain[b] | γ-Chain[b] |
|---|---|---|---|---|---|---|
| Lysine | 76 | 80 | 80 | 33 | 27 | 20 |
| Histidine | 22 | 22 | 22 | 11 | 9 | 2 |
| Arginine | 44 | 46 | 46 | 19 | 14 | 13 |
| Aspartic acid | 129 | 132 | 132 | 57 | 49 | 26 |
| Threonine | 80 | 84 | 84 | 43 | 27 | 14 |
| Serine | 67 | 65 | 65 | 31 | 15 | 19 |
| Glutamic acid | 120 | 116 | 130 | 46 | 50 | 34 |
| Proline | 60 | 58 | 56 | 31 | 11 | 14 |
| Glycine | 66 | 64 | 62 | 33 | 17 | 12 |
| Alanine | 62 | 61 | 59 | 29 | 16 | 14 |
| Cysteine | 15 | 16 | 16 | 7 | 5 | 4 |
| Valine | 102 | 99 | 102 | 49 | 23 | 30 |
| Methionine | 15 | 17 | 18 | 9 | 6 | 3 |

TABLE 2-continued

| | Amino Acid Composition of CVF and its Three Chains. | | | | | |
|---|---|---|---|---|---|---|
| Amino acid | From complete analysis[a] | From gel analysis[b] | Sum of α + β + γ chains[b] | α-Chain[b] | β-Chain[b] | γ-Chain[b] |
| Isoleucine | 77 | 76 | 80 | 29 | 27 | 24 |
| Leucine | 94 | 96 | 98 | 42 | 36 | 20 |
| Tyrosine | 45 | 43 | 36 | 16 | 15 | 5 |
| Phenylalanine | 43 | 43 | 35 | 19 | 9 | 7 |
| Tryptophan | 8 | 8 | 9 | 4 | 3 | 2 |
| Total residues | 1125 | 1126 | 1130 | 508 | 359 | 263 |
| Molecular mass | 126,000 | 126,000 | 126,500 | 57,000 | 40,000 | 29,500 |

[a]Obtained by amino acid analysis of purified CVF.
[b]Obtained by amino acid analysis in a gel slice after SDS-PAGE.
Source: From Vogel and Muller-Eberhard, Immunol. Methods, 73:203–220 (1984)).

From the circular dichroism spectrum, the secondary structure of CVF was derived as 11% α-helix, 47% β-sheet, 18% β-turn, and 24% remainder (Vogel et al., *J. Immunol.*, 133:3235–3241 (1984)). CVF contains three or possibly four N-linked oligosaccharide chains per molecule, but is devoid of O-linked saccharides (Gowda et al., *Mol. Immunol.*, 29:335–342 (1992)). Lectin-affinity blots show that the α- and the β-chain, but not the γ-chain, are glycosylated, and the intensity of staining suggests the presence of more saccharides in the α-chain than in the β-chain (Gowda et al., *Mol. Immunol.*, 29:335–342 (1992)). This is in agreement with the recent finding that the β-chain of CVF, based on its cDNA sequence, contains only one potential N-glycosylation site (Asn-83) (Fritzinger, D. C., Bredehorst, R., and Vogel, C. W., U.S. patent application Ser. No. 08/043,747.

Natural CVF, a snake protein, induces a possibly neutralizing antibody response in humans. In addition, the production of larger quantities of CVF from natural sources is difficult and expensive. It is desirable, therefore, to identify functionally essential regions within the protein molecule to allow for the production of a simplified CVF derivative.

SUMMARY OF THE INVENTION

Accordingly, it is one object of the present invention to provide novel CVF derivatives which are smaller than naturally occurring CVF and retain the complement-activating activity of natural CVF.

It is another object of the present invention to provide a method for preparing such CVF derivatives.

It is another object of the present invention to provide antibody conjugates of such CVF derivatives.

These and other objects, which will become apparent during the following detailed description, have been achieved by the inventors' discovery that CVF derivatives prepared by protease digestion of natural CVF retain the complement-activating activity of natural CVF.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

In a first embodiment, the present invention relates to CVF derivatives which exhibit substantially the same complement-activating activity of natural CVF. By the term "exhibit substantially the same complement-activating activity of natural CVF" it is meant that the CVF derivatives of the present invention induce from 50 to 97%, preferably from 80 to 97% of the level of hemolysis observed with natural CVF as measured by the method of Pickering et al, *Proc. Natl. Acad. Sci. U.S.A.*, 62:521–527 (1969).

Specifically, the CVF derivatives of the present invention are CVF molecules in which from 27 to 210, preferably from 65 to 210, amino acid residues are missing from the β-chain and in which from 6 to 30, preferably 7 to 14, incisions have been made in the β-chain. Preferably, the CVF derivative contains an incision/excision (a cleavage) between amino acids 1449 and 1450 and/or 1450 and 1451 of the CVF β-chain. Other preferred incisions are C-terminal to amino acids Tyr(Y), Phe(F), and Try(W), all of which are found at multiple locations in the C-terminal region of the CVF β-chain. Preferably, both the α-chain and γ-chain are intact, that is, are the same as in natural CVF.

In a second embodiment, the present invention provides a method for preparing such CVF derivatives. In particular, the present CVF derivatives can be prepared by incubating natural CVF with a protease. Suitable proteases include serine proteases such as chymotrypsin and trypsin. Chymotrypsin is the preferred protease. The preferred chymotrypsin is from bovine pancreas, and the preferred trypsin is from swine pancreas. Other types of proteases such as metalloproteases and acid proteases may also be utilized in a similar fashion.

Typically, the incubation is carried out in an aqueous incubation bath at a temperature of 20° to 40° C., preferably 36° to 37.5° C., for a time of 30 to 300 minutes, preferably 60 to 90 minutes. The concentration of the protease in the incubation bath is suitably 0.005 to 5 mg/ml, preferably 0.125 to 1 mg/ml, while the concentration of the CVF is suitably 0.1 to 10 mg/ml, preferably 0.25 to 2 mg/ml. The pH of the bath is suitably 7 to 9, preferably 7.8 to 8.2. The incubation bath may contain, in addition to the protease and CVF, a buffer. Suitable buffers include Tris buffer, phosphate-buffered saline, and veronal buffer. The preferred buffer is Tris buffer. The incubation may be stopped by adding an appropriate protease inhibitor, such as chymostatin, in the case of chymotrypsin, or phenylmethylsulfonylfluoride (PMSF) or 4-(2-aminoethyl)-benzenesulfonylfluoride hydrochloride (AEBSF), in the case of trypsin. Alternatively, the incubation may be halted by cooling the incubation bath, e.g., in an ice bath.

After the incubation is complete, the thus-obtained CVF derivative may be isolated and purified by any conventional techniques including, e.g., size exclusion chromatography, ultrafiltration, etc. The activity of the CVF derivatives may be assayed by the hemolytic assay described in Pickering et al., *Proc. Natl. Acad. Sci. U.S.A.*, 62:521–527 (1969).

It is to be understood that the present process may yield a mixture of products. Thus, the present CVF derivative includes mixtures so long as the mixture exhibits the hemolytic activity described above.

In another embodiment, the present invention relates to antibody conjugates of the present CVF derivatives. The present antibody conjugates may be prepared as described in Vogel and Müller-Eberhard, *Proc. Natl. Acad. Sci. U.S.A.*, 78:7707–7711 (1981); Vogel et al., *Modern Trends in Human Leukemia VI*, Neth et al. eds, Springer Verlag, Berlin, pp. 514–517 (1985); Müller et al., *Br. J. Cancer*, 54:537 (1986); Müller and Müller-Ruchholtz, *Immunology*, 173:195–196 (1986); Müller and Müller-Ruchholtz, *Leukemia Res.*, 11:461–468 (1987); Juhl et al., *Proc. Am. Assoc. Cancer Res.*, 30:392 (1989); Juhl et al., *Mol. Immuno.*, 27:957–964 (1990); and U.S. patent application Ser. No. 08/043,747, which are incorporated herein by reference. Specifically, the present CVF derivative may be conjugated to the antibody by using a crosslinking reagent. Suitable crosslinking reagents include homobifunctional, heterobifunctional, and heterotrifunctional crosslinkers. Preferred crosslinking reagents include N-succinimidyl-3-(2-pyridyldithio)propionate (SPDP), S-(2-thiopyridyl)-L-cysteine hydrazide (TPCH), N-succinimidyl-S-acetylthioacetate (SATA), and extended peptide linkers. The conjugation may be carried out by conventional methods well known to those skilled in the art. Suitable antibodies include antibodies directed against cell surface markers of cancer cells and microorganisms. Preferred antibodies are monoclonal antibodies against highly abundant cell surface antigens on human leukemia cells, human neuroblastoma cells, and human melanoma cells (e.g., R24, 3F8, BW704, etc.).

Since the present CVF derivatives retain the complement activating activity of natural CVF, the present CVF derivatives may be used in any application in which natural CVF is utilized for its complement-activating activity. Thus, the antibody conjugates of the present CVF derivatives may be used for targeting specific cells as described in Vogel and Müller-Eberhard, *Proc. Natl. Acad. Sci. U.S.A.*, 78:7707–7711 (1981); Vogel et al., *Modern Trends in Human Leukemia VI*, Neth et al, eds, Springer Verlag, Berlin, pp. 514–517 (1985); Müller et al., *Br. J. Cancer*, 54:537 (1986); Müller and Müller-Ruchholtz, *Immunology*, 173:195–196 (1986); Müller and Müller-Ruchholtz, *Leukemia Res.*, 11:461–468 (1987); Juhl et al., *Proc. Am. Assoc. Cancer Res.*, 30:392 (1989); Juhl et al., *Mol. Immuno.*, 27:957–964 (1990); and U.S. patent application Ser. No. 08/043,747, which are incorporated herein by reference.

The present CVF derivatives which are devoid of certain parts of the β-chain are less prone to induce a neutralizing anti-CVF immune response.

Other features of the invention will become apparent in the course of the following descriptions of exemplary embodiments which are given for illustration of the invention and are not intended to be limiting thereof.

EXAMPLES

I. Materials and Methods:

A. Purification of CVF.

CVF was purified by preparative chromatography according to published procedures (Vogel and Müller-Eberhard, *J. Immunol. Methods*, 73:203–220 (1984)). A consecutive separation step was performed using a Mono S FPLC column (Pharmacia). The final CVF pool was dialyzed against 0.1M Tris/HCl, pH 8.0, filter-sterilized, and stored at −80° C. until used.

B. CVF activity assay.

The complement activating activity of CVF and of protease-derivatized CVF was determined in a hemolytic assay as described (Pickering et al., *Proc. Natl. Acad. Sci. U.S.A.*, 62:521–527 (1969)). The assay is based on the reactive bystander lysis of guinea pig (gp) erythrocytes after fluid phase activation of the alternative pathway of complement by CVF. A volume of 20 µl of CVF or its derivatives (in various concentrations) was combined with 20 µl of a gp erythrocyte suspension [$5 \times 10^8$ cells/ml in veronal-buffered saline (VBS; 2.5 mM Na-5-5-diethyl barbituric acid, 143 mM NaCl, pH 7.5)] and 20 µl of gp serum. Subsequently, incubation was performed at 37° C. for 30 min. The reaction was stopped by the addition of 1 ml ice cold VBS. Quantification was achieved after 2 min centrifugation of each reaction mixture at 2000 × g by measuring the hemoglobin content in 350 µl of each supernatant in 96-well microtiter plates at a wavelength of 405 nm in an automated ELISA reader (Easy Reader EAR 400 AT, SLT Instruments, Austria). The positive control (100% lysis) was obtained by gp erythrocyte lysis with $H_2O$. Negative controls (0% lysis) were run in VBS without the addition of CVF.

C. Analytical SDS-PAGE.

SDS-PAGE was performed either in a Midget minigel system (Pharmacia) (using separating gels of 9×6×0.75 cm) or in a SE 600 Vertical Slab Unit (Hoefer Scientific Instruments) (using separating gels of 14×16×0.75 cm) according to established methods (Laemmli U.K. *Nature*, 227:680–685 (1970)).

D. Enzymatic digestion of CVF by chymotrypsin.

CVF (1.7 mg/ml in 0.1 M Tris/HCl) was incubated with chymotrypsin (Boehringer; 5 mg/ml in 0.1 M Tris/HCl) at a 1/2 molar ratio for the desired time in a total volume of 1400 µl. All incubations were performed at 37° C. in a shaking incubator. Aliqots of 350 µl were removed after 60, 90, 120, and 150 minutes of incubation. Inactivation of the enzyme was performed as described (Umezawa H., *Meth. Enzymol.*, 45:678–695 (1975)) by rapidly adding 150 µl of the chymotrypsin inhibitor chymostatin [Boehringer; 1 mg/ml in 10% (v/v) DMSO/90% (v/v) 0.1 M Tris/HCl] (molar ratio of enzyme/inhibitor of 2/1).

E. Isolation of chymotrypsin-treated CVF.

Digests of CVF obtained by chymotrypsin treatment were separated by size exclusion chromatography over a Sephadex G-100 column (29×1.5 cm). 400 µl of proteolytically treated CVF were applied to the column and were eluted in 50 mM Tris/HCl, 100 mM NaCl, pH 7.5 at a flow rate of 6 ml/hour. Fractions of the size of 1.5 ml were collected. The resulting peaks were concentrated by ultrafiltration, and buffer was exchanged through passage over a NAP-5 pre-packed column (Pharmacia) in 0.1M Tris/HCl, pH 8.0. Subsequently, fractions were analyzed by CVF activity assay and SDS-PAGE.

Figure 1:
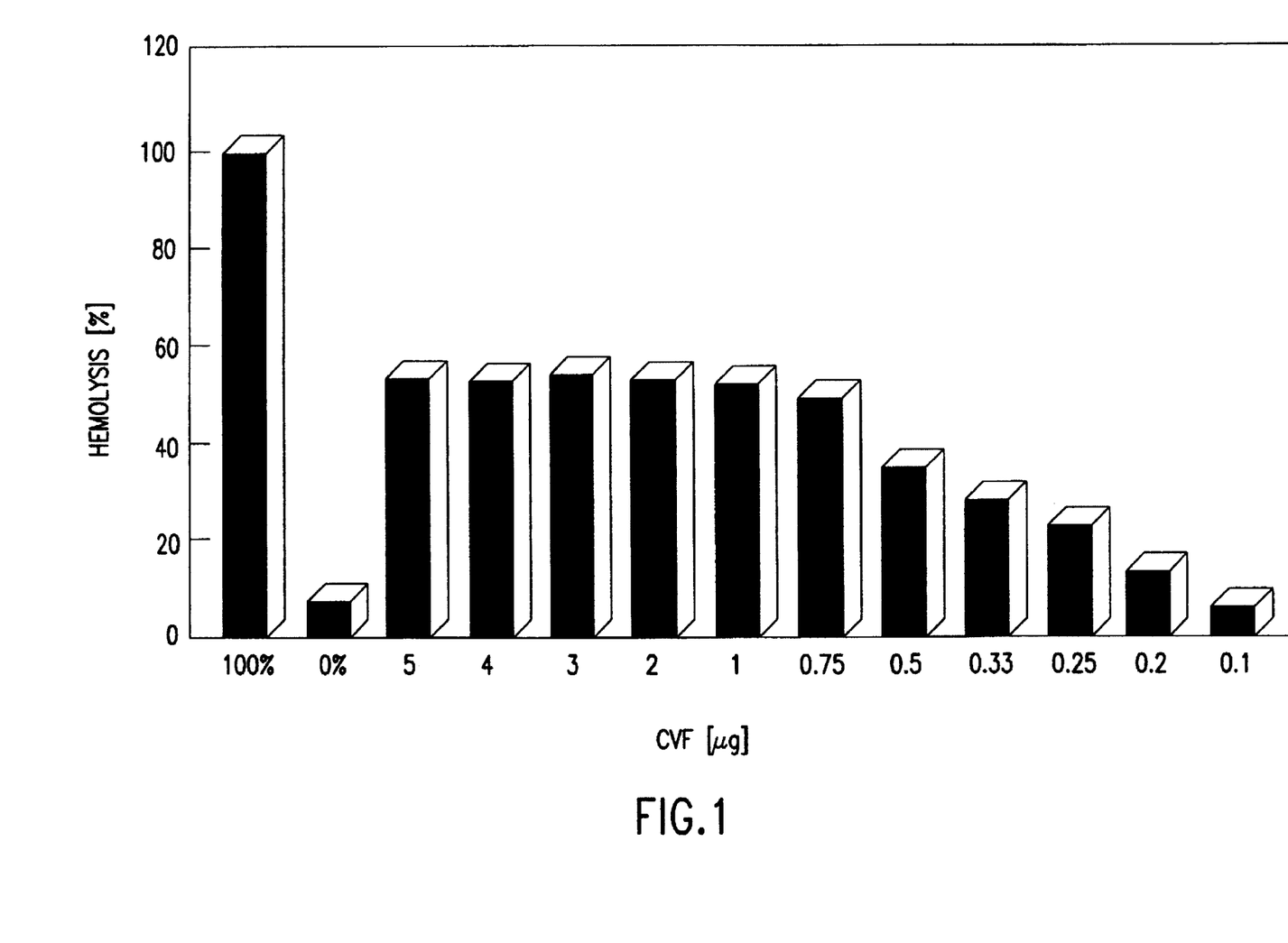
FIG. 1 shows the results of a CVF activity assay. 20 μl of CVF sample were incubated with 20 μl gp erythrocyte suspension and 20 μl gp serum for 30 minutes at 37° C. After the addition of 1 ml ice-cold veronal-buffered saline (VBS) and a centrifugation step, the hemoglobin containing supernatant was analyzed at 405 nm in 96-well microtiter plates using an automated ELISA reader. 100%-control: 20 μl gp erythrocytes + 1040 μl $H_2O$; 0%-control: 20 μl gp serum + 20 μl VBS[++] + 20 μl gp erythrocytes. CVF activity is shown as a function of the amount of CVF added.
Figure 2:
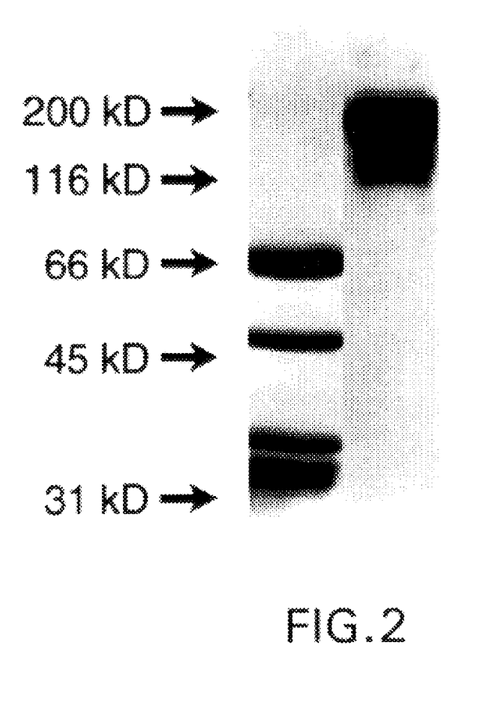
FIG. 2 shows purified CVF as analyzed by 9% (w/v) SDS-PAGE under non-reducing (right panel) and reducing (left panel) conditions. Visualization of protein bands was achieved by silver staining.

II. Results:

FIG. 1 shows a dose-response curve obtained with CVF purified to homogeneity as shown in FIG. 2.

Figure 3:
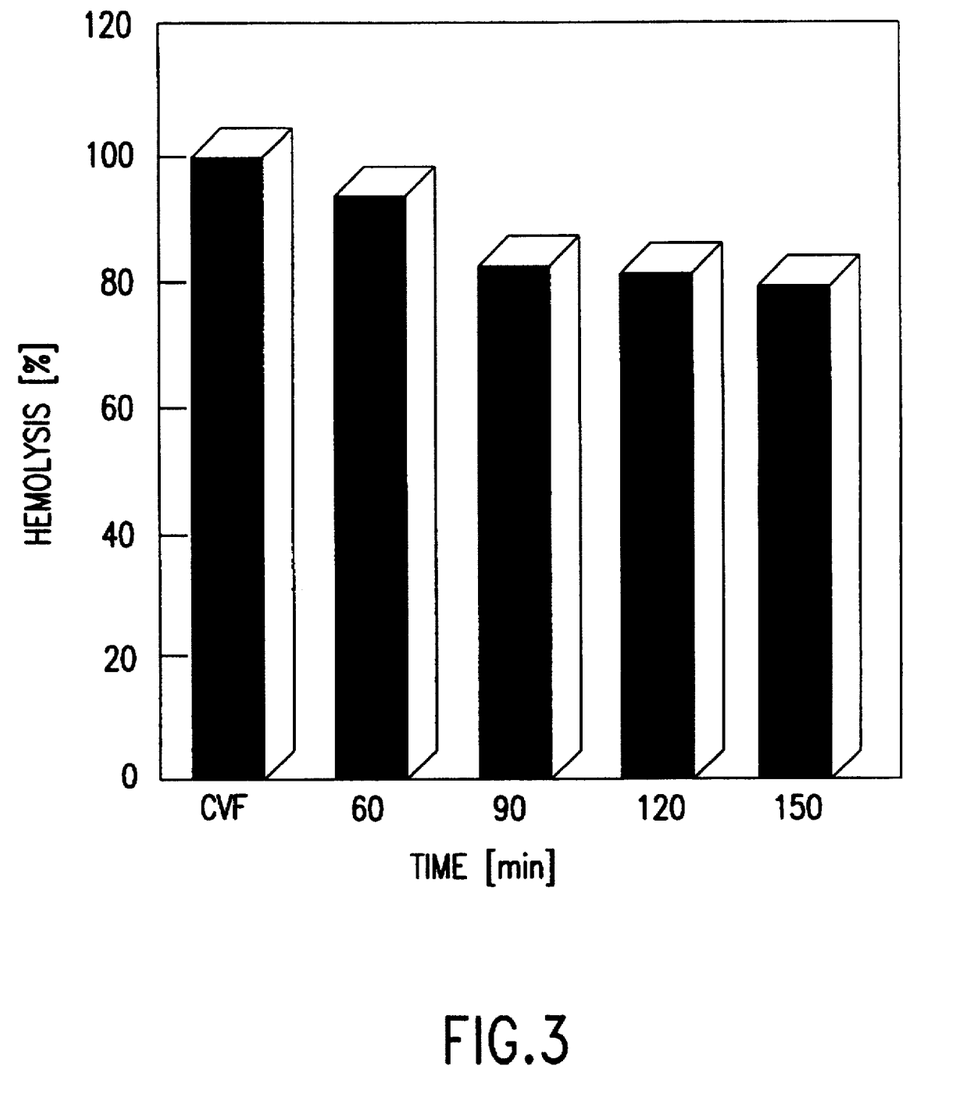
FIG. 3 illustrates the results of an activity assay of chymotrypsin-treated CVF as a function of treatment time. Treatment was performed at a molar ratio of CVF/enzyme of ½ for 60, 90, 120, and 150 minutes at 37° C. The reaction was terminated by the addition of the protease inhibitor chymostatin. 20 μl of CVF sample consisting of an equivalent concentration of 0.037 mg/ml CVF were used. The chymotrypsin/chymostatin control was in the range of the 0%-control as shown in FIG. 1.
Figure 4A:
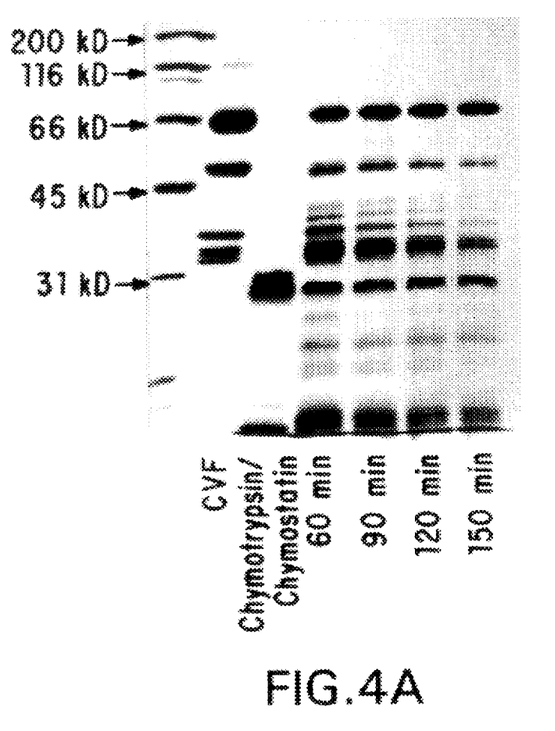
FIG. 4 shows the results of an analysis of chymotrypsin-treated CVF by 12% (w/v) SDS-PAGE. Time-dependent treatment of CVF was performed as described in FIG. 3. The proteolytic digests were separated both under reducing (left panel) and non-reducing (right panel) conditions.
Figure 4B:
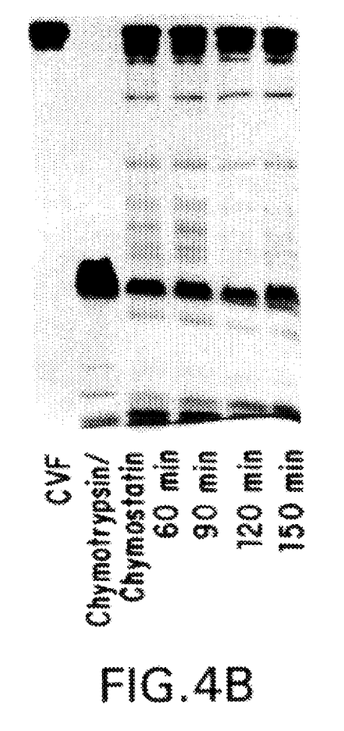

Treatment of CVF with chymotrypsin resulted in no major loss of activity despite the fact that the β-chain of the molecule was gradually digested (FIGS. 3 and 4). Under non-reducing conditions a partial shift in apparent molecular weight was observed indicating the excision of parts of the β-chain (FIG. 4).

Figure 5:
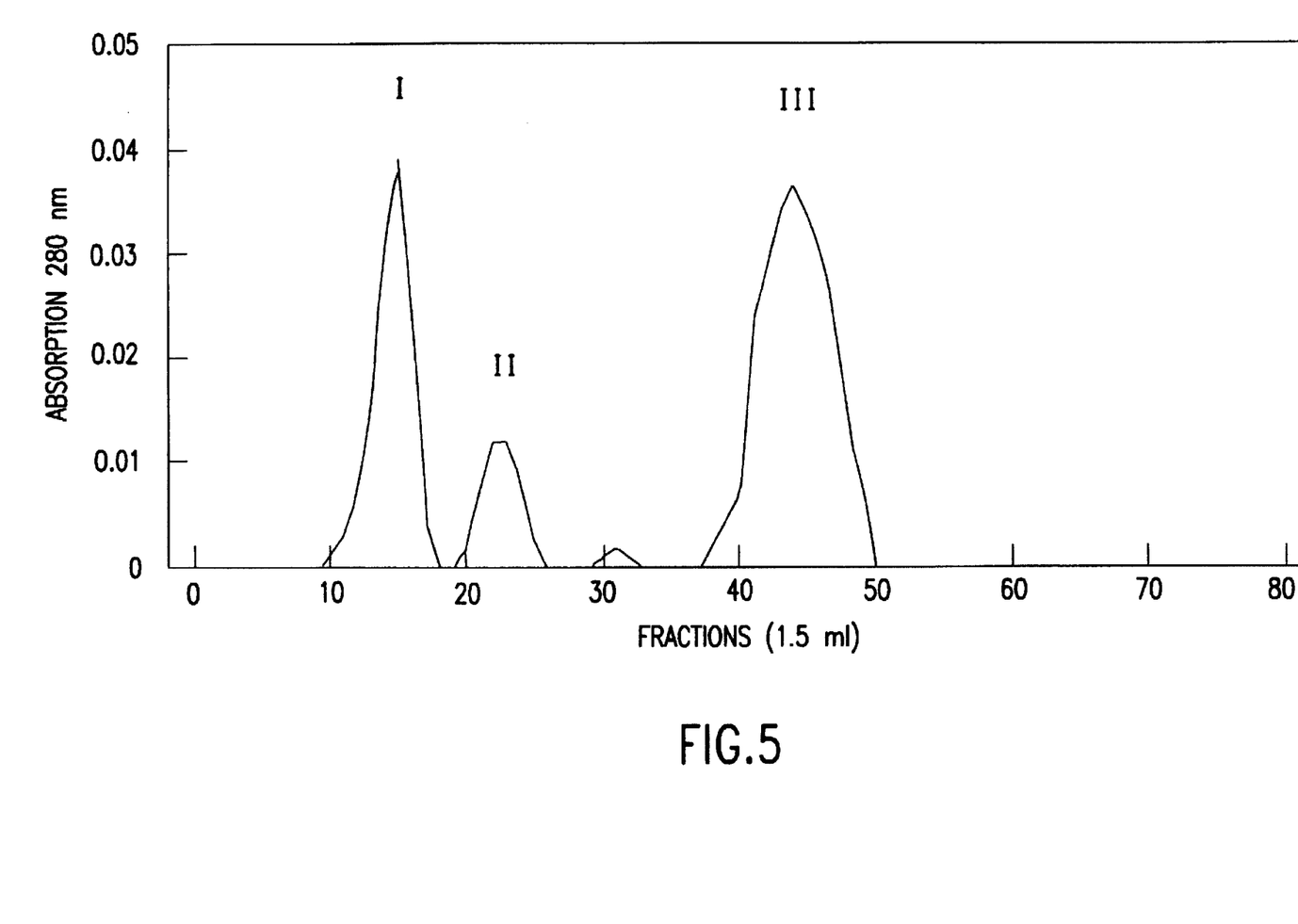
FIG. 5 illustrates the results of purification of chymotrypsin-treated CVF by size exclusion chromatography. Time-dependent treatment of CVF was performed as described in FIG. 3. 400 μl of each CVF/chymotrypsin/chymostatin digest (1 mg/ml CVF; 0.5 mg/ml chymotrypsin; 0.25 mg/ml chymostatin) were applied to Sephadex G-100, and were eluted at a flow rate of 6 ml/hour in 50 mM Tris/HCl, 100 mM NaCl, pH 7.5. Elution profiles typically resulted in three major peaks (designated I, II and III) of which peak I was hemolytically active and analyzed further.
Figure 6:
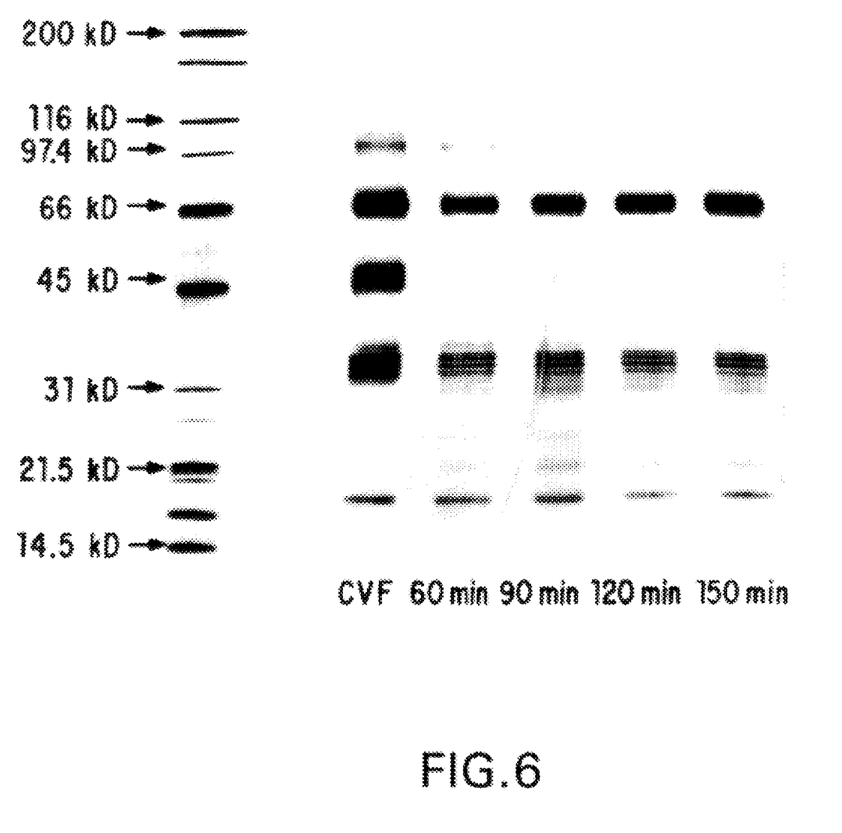
FIG. 6 shows the results of an analysis of purified chymotrypsin-treated CVF (peak I) by 4–20% gradient SDS-PAGE under reducing conditions. Time-dependent treatment of CVF was performed as described in FIG. 3. Purification of chymotrypsin-treated CVF was achieved by gel filtration over Sephadex G-100 as shown in FIG. 5.
Figure 7:
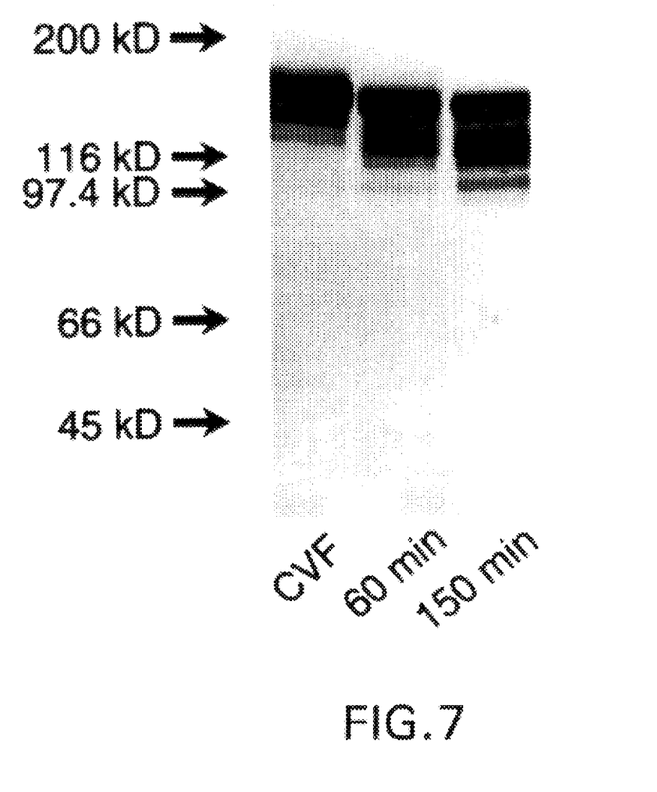
FIG. 7 illustrates the results of an analysis of purified chymotrypsin-treated CVF (peak I) by 4–20% gradient SDS-PAGE under non-reducing conditions. Time-dependent treatment of CVF was performed as described in FIG. 3. Purification of chymotrypsin-treated CVF was achieved by gel filtration over Sephadex G-100 as shown in FIG. 5.
Figure 8:
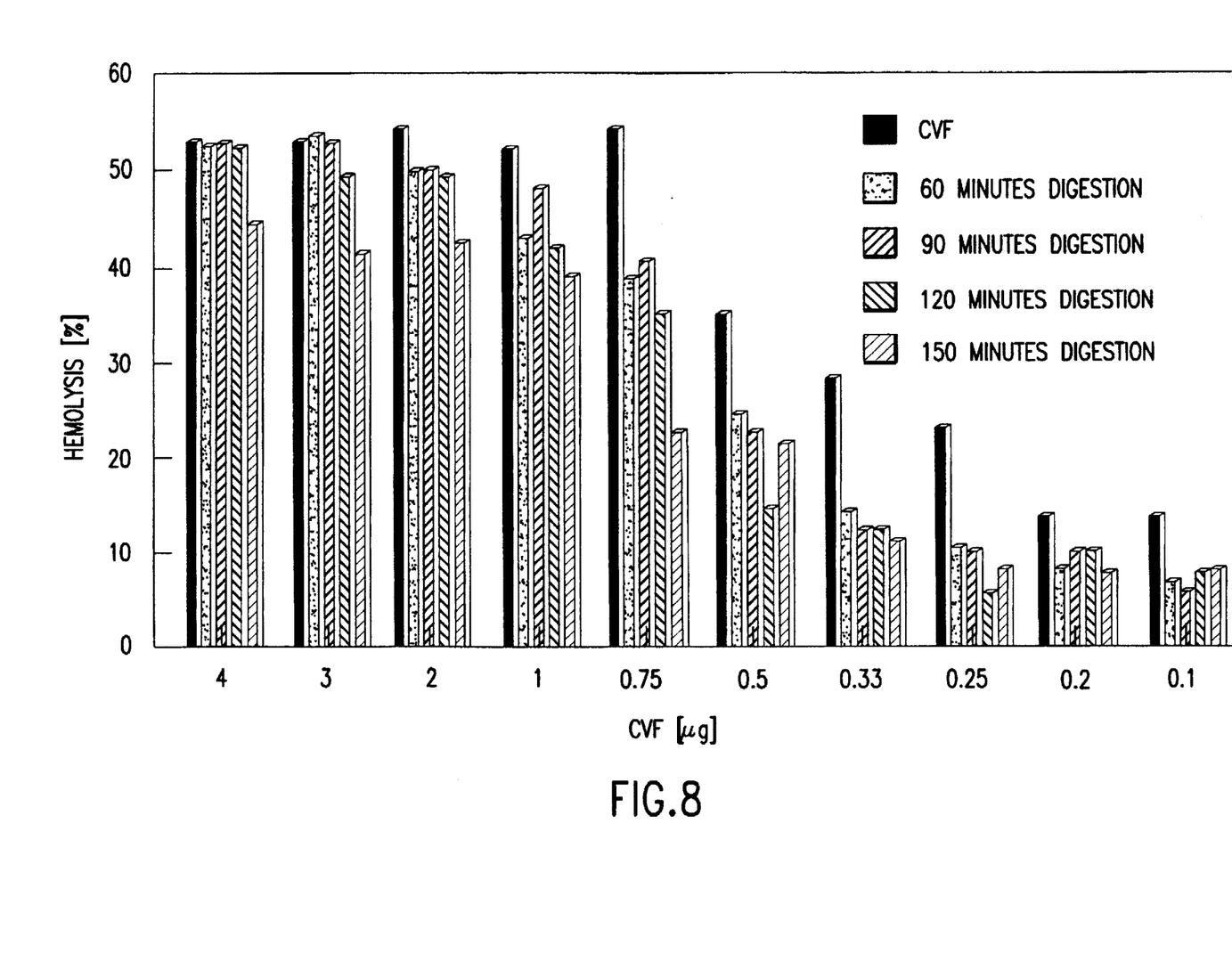
FIG. 8 shows the results of an activity assay of chymotrypsin-treated CVF after purification by size exclusion chromatography. Time-dependent treatment of CVF was performed as described in FIG. 3. Activity is shown as a function of the amount of CVF/CVF derivative added.

After purification of the proteolytically altered CVF by size exclusion chromatography (FIG. 5), the modified molecule was analyzed in more detail. Analysis of peak 1 of the chromatogram confirmed the results provided in FIG. 4. Under reducing SDS-PAGE conditions no intact β-chain could be detected (FIG. 6), and under non-reducing conditions in SDS-PAGE a partial shift to a lower molecular weight was observed (FIG. 7). These data demonstrate that a novel CVF derivative was generated by treatment with chymotrypsin which is characterized (i) by complete disappearance of the intact β-chain when analyzed by SDS-PAGE under reducing conditions, (ii) by a partial shift in the apparent molecular weight on SDS-PAGE under non-reducing conditions, and (iii) by preservation of the biological activity (FIG. 8).

Collectively, these data indicate that CVF has been derivatized by both proteolytic incisions as well as excisions in the β-chain.

Figure 9:
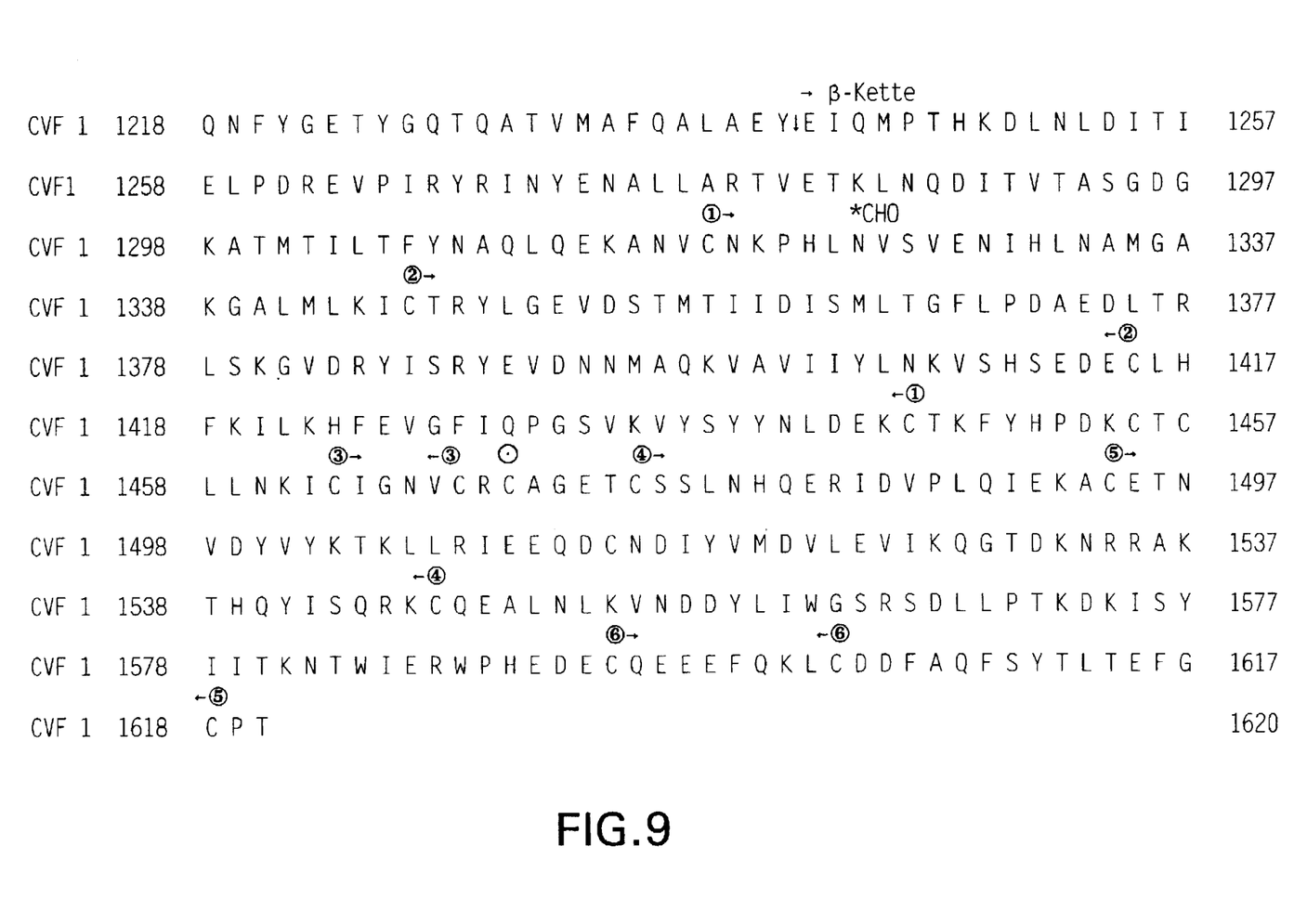
FIG. 9 depicts the potential C-terminal chymotrypsin cleavage sites in the CVF β-chain. The potential C-terminal chymotrypsin cleavage sites are indicated by the bold Y, F, and W residues. The AA-sequence is deduced from the CVF cDNA sequence (Fritzinger D. C., Bredehorst R., Vogel C. W., U.S. patent application Ser. No. 08/043,747). *CHO, potential N-glycosylation site; O, probable position of intrachain disulfide linkages; ⊙, interchain disulfide linkage to CVF γ-chain.
Figure 10:
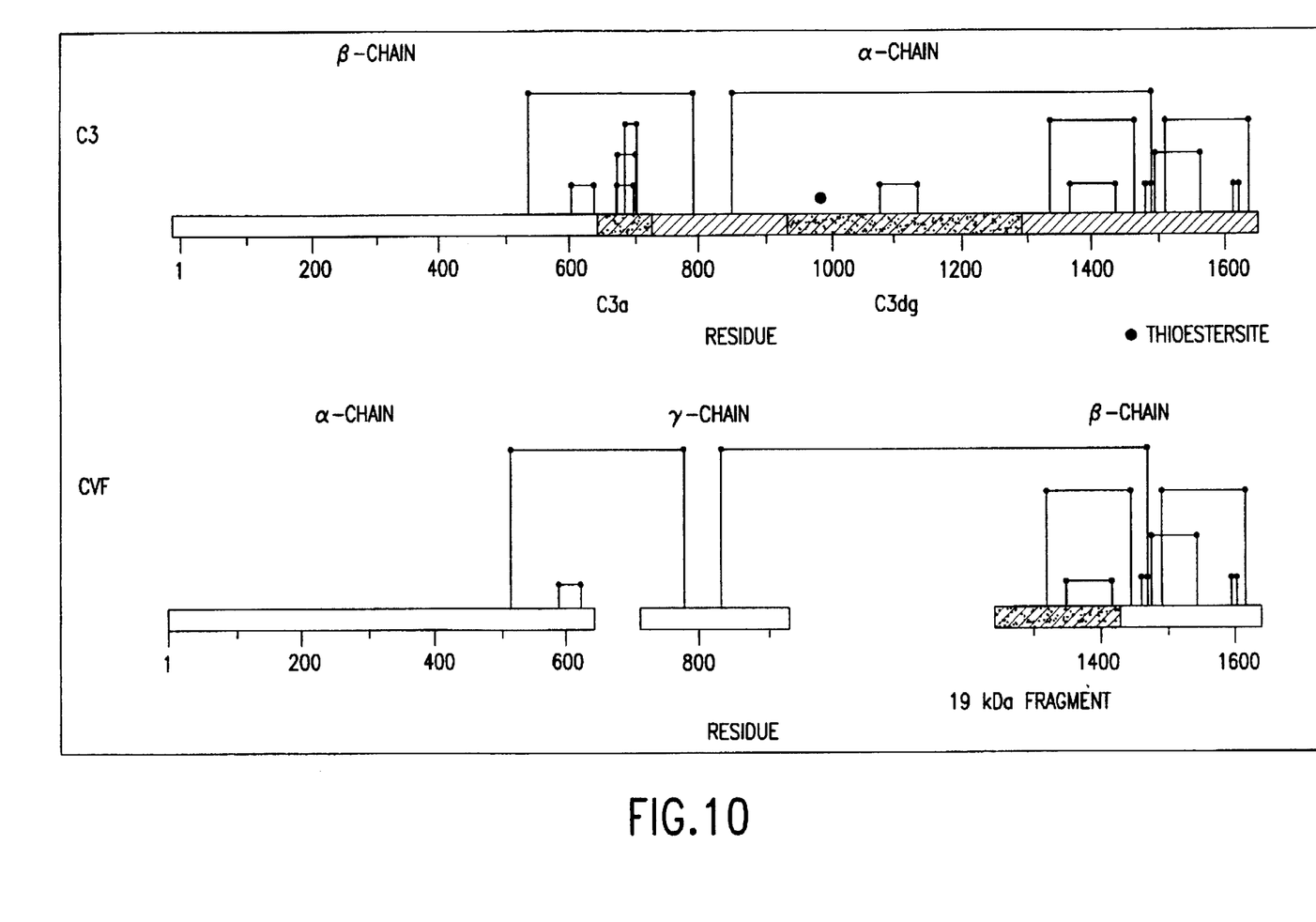
FIG. 10 illustrates an analogy model of CVF disulfide linkages based on the 100% conservation of cysteine residues found in C3 compared to CVF (Dolmer K. and Sottrup-Jensen L., *FEBS Lett.*, 315:85–90 (1993)).

This is in accordance with the amino acid (AA) sequence of the CVF β-chain (SEQ ID NO:1; as deduced from the CVF cDNA) which provides 30 potential cleavage sites for chymotrypsin (FIG. 9). The partial shift in molecular weight of the intact molecule (FIG. 7) can be explained with a disulfide linkage model of CVF (FIG. 10) developed on the basis of the structural analogy of CVF with the complement proteins C3 and C4. All three molecules are characterized by 100% conservation of the cysteine residues throughout evolution. The model illustrates that several incisions in the CVF β-chain can occur without a resulting loss of peptide stands. These molecules are likely to retain their apparent molecular weight, while only molecules which are derivatized by one or more excision steps will show a significantly modified molecular weight.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A cobra venom factor derivative, prepared by a process comprising:
   (a) incubating natural cobra venom factor with a protease for a time of 30 to 300 minutes and at a temperature of 20° to 40° C., to obtain said cobra venom factor derivative;
   wherein said natural cobra venom factor is *Naja naja* cobra venom factor and said protease is chymotrypsin.

2. The cobra venom factor derivative of claim 1, wherein said natural cobra venom factor is incubated with said chymotrypsin in a reaction mixture and said reaction mixture has a pH of from 7 to 9, said natural cobra venom factor is present in said reaction mixture in an amount of 0.1 to 10 mg/ml, and said chymotrypsin is present in said reaction mixture in an amount of 0.005 to 5 mg/ml.

3. The cobra venom factor derivative of claim 2, wherein said reaction mixture comprises a buffer selected from the group consisting of Tris buffer, phosphate-buffered saline, and veronal buffer.

4. The cobra venom factor derivative of claim 1, wherein said incubating is carried out for a time of 60 to 90 minutes.

5. The cobra venom factor derivative of claim 1, wherein said incubating is carried out at a temperature of 36° to 37.5° C.

6. The cobra venom factor derivative of claim 1, wherein said cobra venom factor derivative has a hemolysis activity which is 50 to 97% of the hemolysis activity of said natural cobra venom factor.

7. The cobra venom factor derivative of claim 1, wherein said cobra venom factor derivative has a hemolysis activity which is 80 to 97% of the hemolysis activity of said natural cobra venom factor.

8. The cobra venom factor derivative of claim 1, wherein said chymotrypsin is bovine pancreas chymotrypsin.

9. A process for preparing a cobra venom factor derivative, comprising:
   (a) incubating natural cobra venom factor with a protease for a time of 30 to 300 minutes at a temperature of 20° to 40° C., to obtain said cobra venom factor derivative;
   wherein said natural cobra venom factor is *Naja naja* cobra venom factor and said protease is chymotrypsin.

10. The process of claim 9, wherein said natural cobra venom factor is incubated with said chymotrypsin in a reaction mixture and said reaction mixture has a pH of from 7 to 9, said natural cobra venom factor is present in said reaction mixture in an amount of 0.1 to 10 mg/ml, and said chymotrypsin is present in said reaction mixture in an amount of 0.005 to 5 mg/ml.

11. The process of claim 10, wherein said reaction mixture comprises a buffer selected from the group consisting of Tris buffer, phosphate-buffered saline, and veronal buffer.

12. The process of claim 9, wherein said incubating is carried out for a time of 60 to 90 minutes.

13. The process of claim 9, wherein said incubating is carried out at a temperature of 36° to 37.5° C.

14. The process of claim 9, wherein said cobra venom factor derivative has a hemolysis activity which is 50 to 97% of the hemolysis activity of said natural cobra venom factor.

15. The process of claim 9, wherein said cobra venom factor derivative has a hemolysis activity which is 80 to 97% of the hemolysis activity of said natural cobra venom factor.

16. The process of claim 9, wherein said chymotrypsin is bovine pancreas chymotrypsin.

17. A cobra venom factor derivative, prepared by a process comprising:
   (a) incubating natural cobra venom factor having a β-chain and hemolysis activity with a protease, to obtain said cobra venom factor derivative;
   wherein said natural cobra venom factor having a β-chain is *Naja naja* cobra venom factor and said protease is chymotrypsin and wherein said incubating is carried out under conditions such that said cobra venom factor derivative has a hemolysis activity of 50 to 97% of said hemolysis activity of said natural cobra venom factor and said cobra venom factor derivative does not contain a complete, intact β-chain.

18. The cobra venom factor derivative of claim 17, wherein said incubating is carried out for a time of 30 to 300 minutes and at a temperature of 20° to 40° C.

19. The cobra venom factor derivative of claim 18, wherein said natural cobra venom factor is incubated with said chymotrypsin in a reaction mixture and said reaction mixture has a pH of from 7 to 9, said natural cobra venom factor is present in said reaction mixture in an amount of 0.1 to 10 mg/ml, and said chymotrypsin is present in said reaction mixture in an amount of 0.005 to 5 mg/ml.

20. The cobra venom factor derivative of claim 19, wherein said reaction mixture comprises a buffer selected from the group consisting of Tris buffer, phosphate-buffered saline, and veronal buffer.

21. The cobra venom factor derivative of claim 18, wherein said incubating is carried out for a time of 60 to 90 minutes.

22. The cobra venom factor derivative of claim 18, wherein said incubating is carried out at a temperature of 36° to 37.5° C.

23. The cobra venom factor derivative of claim 18, wherein said cobra venom factor derivative has a hemolysis activity which is 80 to 97% of the hemolysis activity of said natural cobra venom factor.

24. The cobra venom factor derivative of claim 18, wherein said chymotrypsin is bovine pancreas chymotrypsin.

25. A process for preparing a cobra venom factor derivative, comprising:
   (a) incubating natural cobra venom factor having a β-chain and hemolysis activity with a protease, to obtain said cobra venom factor derivative;
   wherein said natural cobra venom factor having a β-chain is *Naja naja* cobra venom factor and said protease is chymotrypsin, and said incubating is carried out such that said cobra venom factor derivative has a hemolysis activity of 50 to 97% of said hemolysis activity of said natural cobra venom factor and said cobra venom factor derivative does not contain a complete, intact β-chain.

26. The process of claim 25, wherein said natural cobra venom factor is incubated with said chymotrypsin in a reaction mixture and said reaction mixture has a pH of from 7 to 9, said natural cobra venom factor is present in said reaction mixture in an amount of 0.1 to 10 mg/ml, and said chymotrypsin is present in said reaction mixture in an amount of 0.005 to 5 mg/ml.

27. The process of claim 26, wherein said reaction mixture comprises a buffer selected from the group consisting of Tris buffer, phosphate-buffered saline, and veronal buffer.

28. The process of claim 25, wherein said incubating is carried out for a time of 30 to 300 minutes and at a temperature of 20° to 40° C.

29. The process of claim 25, wherein said incubating is carried out for a time of 60° to 90 minutes and at a temperature of 36 to 37.5° C.

30. The process of claim 25, wherein said cobra venom factor derivative has a hemolysis activity which is 80 to 97% of the hemolysis activity of said natural cobra venom factor.

31. The process of claim 25, wherein said chymotrypsin is bovine pancreas chymotrypsin.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 403 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:1:

-continued

```
Gln Asn Phe Tyr Gly Glu Thr Tyr Gly Gln Thr Gln Ala Thr Val Met
1               5               10              15
Ala Phe Gln Ala Leu Ala Glu Tyr Glu Ile Gln Met Pro Thr His Lys
        20              25              30
Asp Leu Asn Leu Asp Ile Thr Ile Glu Leu Pro Asp Arg Glu Val Pro
        35              40              45
Ile Arg Tyr Arg Ile Asn Tyr Glu Asn Ala Leu Leu Ala Arg Thr Val
    50              55              60
Glu Thr Lys Leu Asn Gln Asp Ile Thr Val Thr Ala Ser Gly Asp Gly
65              70              75              80
Lys Ala Thr Met Thr Ile Leu Thr Phe Tyr Asn Ala Gln Leu Gln Glu
                85              90              95
Lys Ala Asn Val Cys Asn Lys Pro His Leu Asn Val Ser Val Glu Asn
            100             105             110
Ile His Leu Asn Ala Met Gly Ala Lys Gly Ala Leu Met Leu Lys Ile
        115             120             125
Cys Thr Arg Tyr Leu Gly Glu Val Asp Ser Thr Met Thr Ile Ile Asp
    130             135             140
Ile Ser Met Leu Thr Gly Phe Leu Pro Asp Ala Glu Asp Leu Thr Arg
145             150             155             160
Leu Ser Lys Gly Val Asp Arg Tyr Ile Ser Arg Tyr Glu Val Asp Asn
                165             170             175
Asn Met Ala Gln Lys Val Ala Val Ile Ile Tyr Leu Asn Lys Val Ser
            180             185             190
His Ser Glu Asp Glu Cys Leu His Phe Lys Ile Leu Lys His Phe Glu
        195             200             205
Val Gly Phe Ile Gln Pro Gly Ser Val Lys Val Tyr Ser Tyr Tyr Asn
    210             215             220
Leu Asp Glu Lys Cys Thr Lys Phe Tyr His Pro Asp Lys Cys Thr Cys
225             230             235             240
Leu Leu Asn Lys Ile Cys Ile Gly Asn Val Cys Arg Cys Ala Gly Glu
                245             250             255
Thr Cys Ser Ser Leu Asn His Gln Glu Arg Ile Asp Val Pro Leu Gln
            260             265             270
Ile Glu Lys Ala Cys Glu Thr Asn Val Asp Tyr Val Tyr Lys Thr Lys
        275             280             285
Leu Leu Arg Ile Glu Glu Gln Asp Cys Asn Asp Ile Tyr Val Met Asp
    290             295             300
Val Leu Glu Val Ile Lys Gln Gly Thr Asp Lys Asn Arg Arg Ala Lys
305             310             315             320
Thr His Gln Tyr Ile Ser Gln Arg Lys Cys Gln Glu Ala Leu Asn Leu
                325             330             335
Lys Val Asn Asp Asp Tyr Leu Ile Trp Gly Ser Arg Ser Asp Leu Leu
            340             345             350
Pro Thr Lys Asp Lys Ile Ser Tyr Ile Ile Thr Lys Asn Thr Trp Ile
        355             360             365
Glu Arg Trp Pro His Glu Asp Glu Cys Gln Glu Glu Phe Gln Lys
    370             375             380
Leu Cys Asp Asp Phe Ala Gln Phe Ser Tyr Thr Leu Thr Glu Phe Gly
385             390             395             400
Cys Pro Thr
```